US010805553B2

United States Patent
Kudo et al.

(10) Patent No.: US 10,805,553 B2
(45) Date of Patent: Oct. 13, 2020

(54) IMAGING APPARATUS AND IMAGING METHOD

(71) Applicant: CANON KABUSHIKI KAISHA, Tokyo (JP)

(72) Inventors: Yuma Kudo, Kawasaki (JP); Junya Fukumoto, Yokohama (JP); Takashi Tsuda, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 28 days.

(21) Appl. No.: 15/952,709

(22) Filed: Apr. 13, 2018

(65) Prior Publication Data
US 2018/0302571 A1 Oct. 18, 2018

(30) Foreign Application Priority Data

Apr. 14, 2017 (JP) .................................. 2017-080576
Apr. 12, 2018 (JP) .................................. 2018-076696

(51) Int. Cl.
| | | |
|---|---|---|
| H04N 5/235 | (2006.01) |
| H04N 5/243 | (2006.01) |
| H04N 5/272 | (2006.01) |
| A61B 5/00 | (2006.01) |
| H04N 9/04 | (2006.01) |
| H04N 9/09 | (2006.01) |
| H04N 5/232 | (2006.01) |
| H04N 5/33 | (2006.01) |

(52) U.S. Cl.
CPC .......... *H04N 5/243* (2013.01); *A61B 5/0059* (2013.01); *A61B 5/0071* (2013.01); *A61B 5/7425* (2013.01); *H04N 5/2353* (2013.01); *H04N 5/2354* (2013.01); *H04N 5/23232* (2013.01); *H04N 5/272* (2013.01); *H04N 5/332* (2013.01); *H04N 9/045* (2013.01); *H04N 9/09* (2013.01)

(58) Field of Classification Search
CPC .................................. A16B 6/52; H04N 5/235
USPC ............................................... 348/221.1, 362
See application file for complete search history.

(56) References Cited

U.S. PATENT DOCUMENTS

| | | | | |
|---|---|---|---|---|
| 8,721,532 B2 * | 5/2014 | Takei | ................. | G02B 23/2461 600/109 |
| 2007/0073104 A1 | 3/2007 | Iketani et al. | | |
| 2009/0036743 A1 * | 2/2009 | Yabe | .................. | A61B 1/00009 600/180 |

(Continued)

FOREIGN PATENT DOCUMENTS

| | | |
|---|---|---|
| JP | 4761899 | 8/2011 |
| JP | 5265055 | 8/2013 |

*Primary Examiner* — Anthony J Daniels
(74) *Attorney, Agent, or Firm* — Venable LLP (57) ABSTRACT

According to one embodiment, an imaging apparatus includes an image sensor, image generation circuitry, calculation circuitry and superimposition circuitry. The image generation circuitry successively generates a first image and a second image. The calculation circuitry calculates a first parameter to allow brightness of the first image to be equal to or close to a predetermined value, and calculates a second parameter relating to brightness of the second image based on the first parameter and a predetermined ratio. The superimposition circuitry generates a composite image by superimposing the second image in which the brightness is adjusted using the second parameter onto the first image in which the brightness is adjusted using the first parameter.

13 Claims, 5 Drawing Sheets

(56) References Cited

U.S. PATENT DOCUMENTS

| | | | |
|---|---|---|---|
| 2009/0289200 A1* | 11/2009 | Ishii | A61B 1/00009 250/459.1 |
| 2011/0237895 A1* | 9/2011 | Yoshida | A61B 1/00009 600/180 |
| 2012/0078044 A1* | 3/2012 | Yamaguchi | A61B 1/045 600/109 |
| 2012/0328175 A1* | 12/2012 | Watanabe | A61B 1/00009 382/132 |
| 2013/0150728 A1 | 6/2013 | Takei et al. | |
| 2015/0173595 A1* | 6/2015 | Takekoshi | A61B 1/00009 600/317 |
| 2016/0157722 A1* | 6/2016 | Kubo | A61B 1/00009 600/476 |

* cited by examiner

IMAGING APPARATUS AND IMAGING METHOD

CROSS-REFERENCE TO RELATED APPLICATIONS

This application is based upon and claims the benefit of priority from the prior Japanese Patent Application No. 2017-080576, filed Apr. 14, 2017, and No. 2018-076696, filed Apr. 12, 2018, the entire contents of all of which are incorporated herein by reference.

FIELD

Embodiments described herein relate generally to an imaging apparatus and an imaging method.

BACKGROUND

In the case where a subject is observed by using a white light source that emits visible light (normal observation), the sensitivity (exposure time, amplification amount, etc.) is automatically controlled in accordance with the brightness of the background (incident light amount level from the white light source) to maintain uniform brightness. In the case where fluorescence emitted from a subject due to application of X-rays, ultraviolet rays, infrared rays, or visible light as excitation light is observed (fluorescence observation), similar automatic control of the sensitivity is performed.

For example, in the medical field, there is a case where an image in which an image obtained by the aforementioned fluorescence observation (fluorescent image) is superimposed to an image obtained by the normal observation (background image) is observed. In this case, the sensitivity of the background image is automatically controlled; however, the sensitivity of the fluorescent image cannot be automatically controlled since the position or the amount of the fluorescence parts to be displayed cannot be specified, and accordingly, the sensitivity has to be set manually by a user.

However, it is generally observed in the medical field that after the user sets the sensitivity of the fluorescent image, the irradiation conditions change, for example, the light amount changes due to changes in the distance between the light source and a subject or the irradiation angle to the subject.

If the irradiation conditions change, the sensitivity of the background image is maintained at the constant level by the automatic control; however, the sensitivity of the fluorescent image is not automatically controlled. Accordingly, the user needs to set the sensitivity of the fluorescent image in comparison with the brightness of the background image every time the irradiation conditions change, which is laborious and burdensome.

DETAILED DESCRIPTION

In general, according to one embodiment, an imaging apparatus includes an image sensor, image generation circuitry, calculation circuitry and superimposition circuitry. The image sensor generates a first electrical signal upon receiving first light, and generates a second electrical signal upon receiving second light. The image generation circuitry successively generates a first image based on the first electrical signal, and successively generates a second image based on the second electrical signal. The calculation circuitry calculates a first control parameter value to allow brightness of the first image to be equal to or close to a predetermined value, and calculates a second control parameter value relating to brightness of the second image based on the first control parameter value and a predetermined ratio. The superimposition circuitry generates a composite image by superimposing the second image in which the brightness is adjusted using the second control parameter value onto the first image in which the brightness is adjusted using the first control parameter value.

In the following descriptions, an imaging apparatus and an imaging method according to the present embodiments will be described with reference to the drawings. In the embodiments described below, elements assigned with the same reference symbols perform the same operations, and redundant descriptions thereof will be omitted as appropriate.

First Embodiment

The imaging apparatus according to the first embodiment will be explained with reference to the block diagram of FIG. 1.

An imaging apparatus 1 according to the first embodiment includes imaging circuitry 11, image processing circuitry 13, image generation circuitry 15, image superimposition circuitry 17, a white light source 20, and an IR source 22.

The imaging circuitry 11 includes a prism 111, shutters 112, 113, 114, and 115, and image sensors 116, 117, 118, and 119.

The image processing circuitry 13 includes gain adjustment circuitry 131, 132, and 133, master gain circuitry 134, evaluation calculation circuitry 135, sensitivity calculation circuitry 136, background sensitivity control circuitry 137, adding circuitry 138, and fluorescence sensitivity control circuitry 139.

The white light source 20 emits white light which is a visible light in which light beams of various wavelengths are mixed. The emitted white light is applied to a subject P. The white light applied to the subject P reflects and reflective light is generated.

The IR source 22 outputs near infrared excitation light (hereinafter referred to as IR (infrared rays) light). The output IR light is applied to the subject P. The case where the subject P includes a fluorescent substance that is excited by IR light is assumed here. Fluorescence is generated from the fluorescent substance.

The prism 111 is, for example, a dichroic prism which splits the reflective light and fluorescence from the subject P into three primary colors light, R (red) light, G (green) light, and B (blue) light. With the dichroic prism, fluorescence is split into the same path as R light. Accordingly, the shutter 112 and the image sensor 116 are commonly used for R light and fluorescence, and they are processed in a time-division manner. However, the drawings virtually illustrate that R light and fluorescence are processed in separate paths for simplification of the explanation.

Figure 1:
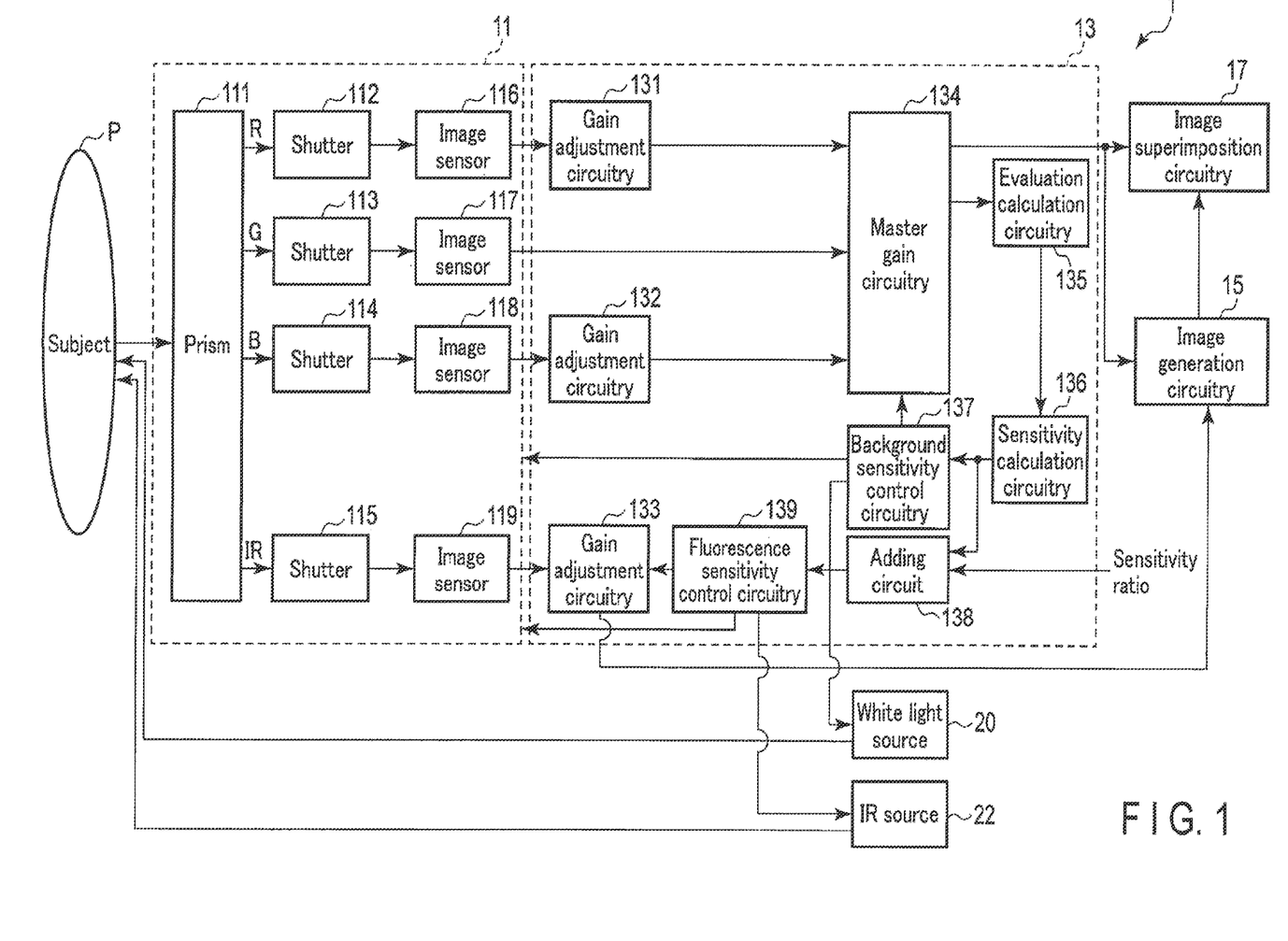
FIG. 1 is a block diagram of an imaging apparatus according to the first embodiment.

That is, as shown in FIG. 1, it is explained that R light passes through the shutter 112 and is received at the image sensor 116 during the time period when the white light enters the prism 111, and fluorescence passes through the shutter 115 and is received at the image sensor 119 during the time period when fluorescence enters the prism 111, in the manner that the paths are virtually divided. An example of the time division control will be described with reference to FIG. 3.

The shutter 112 adjusts the incident light amount (hereinafter referred to as exposure time) when the R light split by the prism 111 enters the image sensor 116, which is a post-processing element.

The shutter 113 adjusts the exposure time when the G light split by the prism 111 enters the image sensor 117, which is a post-processing element.

The shutter 114 adjusts the exposure time when the B light split by the prism 111 enters the image sensor 118, which is a post-processing element.

The shutter 115 adjusts the exposure time when the IR light split by the prism 111 enters the image sensor 119, which is a post-processing element.

In the case where each of the shutters is a mechanical shutter, the shutters adjust the incident light amount relative to the image sensors by being physically open or closed. That is, in the case where the mechanical shutters are adopted, the "exposure time" indicates the time period during which the image sensor is receiving light.

On the other hand, in the case where each of the shutters is an electronic shutter, the shutters adjust the incident light amount relative to the image sensors by adjusting the amount of charge from the state where a capacitor is empty. That is, in the case where the electronic shutters are adopted, the "exposure time" indicates the time period for re-charging after the charge is discarded.

The image sensor 116 performs photoelectric conversion to the R light and generates an R-imaging signal that is an electrical signal.

The image sensor 117 performs photoelectric conversion to the G light and generates a G-imaging signal that is an electrical signal.

The image sensor 118 performs photoelectric conversion to the B light and generates a B-imaging signal that is an electrical signal. In the following description, the R-imaging signal, G-imaging signal, and B-imaging signal are also referred integrally to as RGB imaging signals that are electrical signals obtained by receiving white light.

The image sensor 119 performs photoelectric conversion to the IR light and generates an IR imaging signal that is an electrical signal.

The case where a CCD (Charge-Coupled Device) image sensor may be adopted for the image sensors, for example, is assumed. However, other imaging devices such as a CMOS (Complementary Metal-Oxide Semiconductor), etc. may be adopted.

Although it is not illustrated in the drawings, an excitation light filter that blocks excitation light is provided in the imaging circuitry 11. With this structure, IR light does not enter the image sensor 119; only fluorescence components can enter the image sensor 119.

The gain adjustment circuitry 131 receives an R-imaging signal from the image sensor 116 and adjusts a gain of the R-imaging signal.

The gain adjustment circuitry 132 receives a B-imaging signal from the image sensor 118 and adjusts a gain of the B-imaging signal.

The gain adjustment by the gain adjustment circuitry 131 and 132 is so-called white balance adjustment, and it is sufficient that a gain is adjusted by adjusting the amplitude of the R-imaging signal and the B-imaging signal if required, by adopting the general processing.

The gain adjustment circuitry 133 respectively receives an IR imaging signal from the image sensor 119, and a control signal relating to the sensitivity of a fluorescent image (hereinafter referred to as a fluorescence sensitivity) generated based on the IR imaging signal from an adding circuit 138 described later. The gain adjustment circuitry 133 adjusts a gain of the IR imaging signal based on the control signal.

The master gain circuitry 134 respectively receives an R-imaging signal from the gain adjustment circuitry 131, a G-imaging signal from the image sensor 117, and a B-imaging signal from the gain adjustment circuitry 132, and adjusts the gains of the R-imaging signal, G-imaging signal, and B-imaging signal.

The evaluation calculation circuitry 135 receives from the master gain circuitry 134 the R-imaging signal, G-imaging signal, and B-imaging signal in which the gain is adjusted, and calculates an evaluation value relating to the brightness of the background image which is a color image based on the R-imaging signal, G-imaging signal, and B-imaging signal. The evaluation value is, for example, brightness value of a pixel.

The sensitivity calculation circuitry 136 receives the evaluation value from the evaluation calculation circuitry 135, and compares the evaluation value with a predetermined target value to calculate a set value (control parameter value) of the sensitivity of the background image (hereinafter referred to as background sensitivity). For example, if the evaluation value is greater than the target value of brightness, the background sensitivity is set so that the brightness of the image decreases, and if the evaluation value is less than the target value, the background sensitivity is set so that the brightness of the image increases.

The background sensitivity control circuitry 137 receives the set background sensitivity from the sensitivity calculation circuitry 136, determines which of the gain, the exposure time, or the light amount is used to control the background sensitivity, and generates a control signal corresponding to the determined control means.

The adding circuit 138 respectively receives the set background sensitivity from the sensitivity calculation circuitry 136, and a sensitivity ratio set by the user from outside, and calculates a set value (control parameter value) of the sensitivity of the fluorescent image (hereinafter referred to as fluorescence sensitivity) based on the IR imaging signal, by using the background sensitivity and the sensitivity ratio.

The fluorescence sensitivity control circuitry 139 receives the calculated set value of the fluorescence sensitivity from the adding circuit 138, determines which of the gain, the exposure time, or the light amount is used to control the fluorescence sensitivity, and generates a control signal corresponding to the determined control means.

The image generation circuitry 15 successively receives the R-imaging signal, the G-imaging signal, and the B-imaging signal from the master gain circuitry 134, and the IR imaging signal from the gain adjustment circuitry 133, upon generation of these signals. The image generation circuitry 15 successively generates the background image based on the R-imaging signal, the G-imaging signal, and the B-imaging signal, and the fluorescent image based on the IR imaging signal.

The image superimposition circuitry 17 combines the background image and the fluorescent image by a blending, etc. to generate a composite image. As a result, an image in which fluorescence components are superimposed on the background image is obtained, and the image is displayed on a display (not illustrated) such as a monitor, etc.

Figure 2:
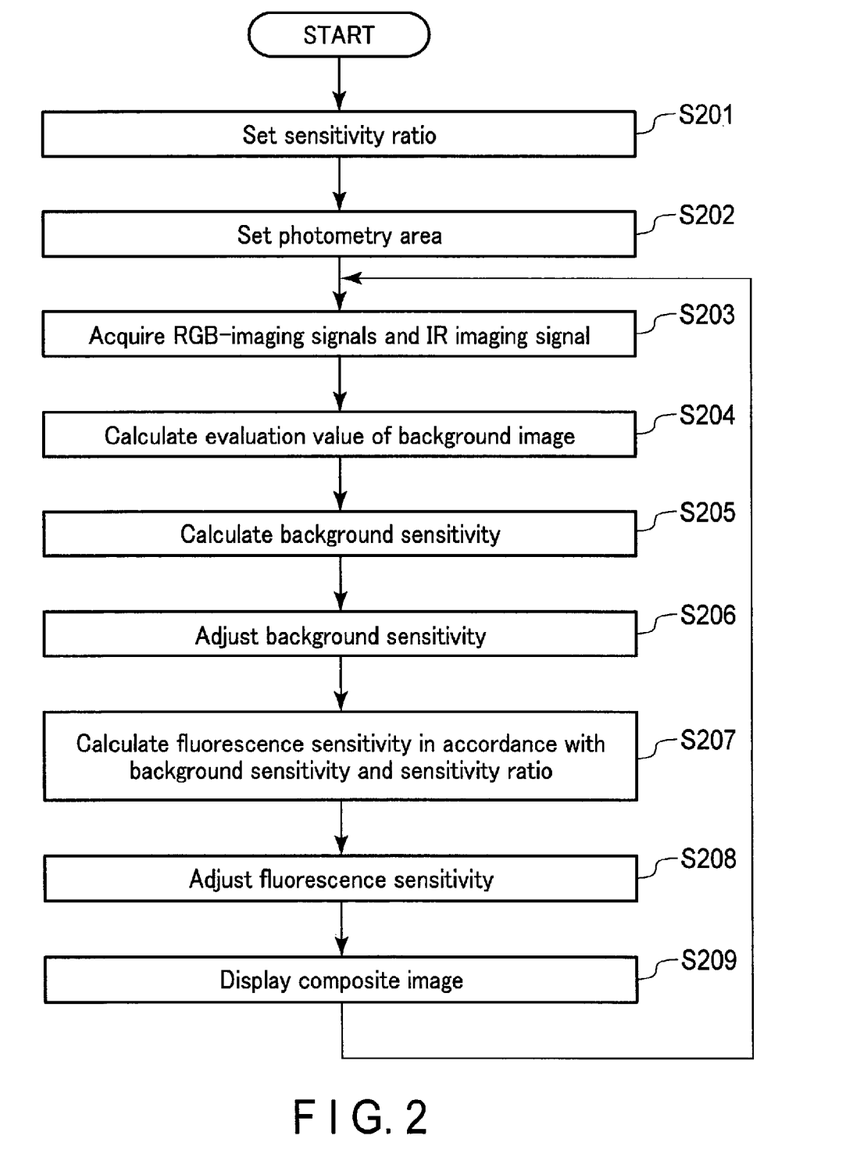
FIG. 2 is a flowchart of sensitivity control processing of the imaging apparatus according to the first embodiment.

The sensitivity control processing of the imaging apparatus 1 according to the first embodiment will be explained with reference to the flowchart of FIG. 2.

The operation of the imaging apparatus 1 is explained, assuming that each imaging signal is successively acquired at predetermined sampling timings so that a composite image based on each imaging signal can be displayed as a movie at 60 fps, for example. A still image may be acquired instead of a movie.

In step S201, the sensitivity ratio is set. The image processing circuitry 13 may acquire a predetermined default value as the sensitivity ratio. Alternatively, a composite image is generated by using the default value as the sensitivity ratio, and the user adjusts the composite image displayed on the display by using a dial or a mouse so that the fluorescent parts have the brightness suitable for being viewed in contrast to the background. Thereafter, the user presses an enter button, for example, to set the ratio between the background sensitivity and the fluorescence sensitivity at a particular time phase when the entered image is acquired as the sensitivity ratio.

In step S202, a photometry area is set. The image processing circuitry 13 may acquire an area manually set by the user as the photometry area. Alternatively, the image processing circuitry 13 may use an area which is preset in the shape and the size relative to an image as the photometry area.

In step S203, the imaging circuitry 11 acquires the R-imaging signal, the G-imaging signal, the B-imaging signal, and the IR imaging signal.

In step S204, the evaluation calculation circuitry 135 calculates the evaluation value of the background image. The range that the brightness is evaluated in the background image may be the entire background image, or the photometry area set in step S202. The brightness of the background image may be an average of the brightness values of each pixel, or an integration of the maximum RGB pixel values.

In step S205, the sensitivity calculation circuitry 136 calculates the background sensitivity. The background sensitivity calculated in this step may be expressed by "exposure time×master gain value".

In step S206, the background sensitivity control circuitry 137 determines a control means of the background sensitivity based on the obtained background sensitivity. The background sensitivity is adjusted in accordance with the determined control means.

For example, in the case where the gain is controlled, the background sensitivity control circuitry 137 transmits to the master gain circuitry 134 a control signal to control the gain so that the background sensitivity is equal to or close to the set value Sw of the background sensitivity. The master gain circuitry 134 controls the gains of the R-imaging signal, G-imaging signal, and B-imaging signal based on the control signal.

In the case where the exposure time is controlled, the background sensitivity control circuitry 137 transmits to the imaging circuitry 11 a control signal to control the exposure time so that the background sensitivity is equal to or close to the set value Sw of the background sensitivity. The shutters 112, 113, and 114 of the imaging circuitry 11 control the exposure time in accordance with the control signal. Specifically, the opening or closing time is controlled if the shutters are mechanical shutters, and the amount of charge is controlled if the shutters are electronic shutters.

In the case where the light amount is controlled, the background sensitivity control circuitry 137 transmits to the white light source 20 a control signal to control the light amount to be equal to or close to the set value Sw of the background sensitivity. The white light source 20 emits light of the amount controlled in accordance with the control signal.

In the case where the background sensitivity is adjusted by a certain control means, there may be a case where the background sensitivity cannot be approximate to the set value Sw, and the background sensitivity cannot be further adjusted by the certain control means. For example, in the case where the background sensitivity is attempted to be adjusted by controlling the gain, there may be a case where the gain cannot be increased any more. In such a case, the background sensitivity may be adjusted by adopting another control means in combination, for example, by controlling the shutters 112, 113, and 114 of the imaging circuitry 11 to extend the exposure time.

In the case where the background sensitivity is increased (brightening the background image), the shutters 112, 113, and 114 are first controlled to extend the exposure time. If the brightness is not sufficient after the control of the shutters, it is desired that the master gain circuitry 134 controls the gain to be increased. However, it may be possible to control the gain prior to the control of the shutters.

In step S207, the adding circuit 138 calculates the set value of the fluorescence sensitivity in accordance with the set value Sw of the background sensitivity calculated in step S206 and the sensitivity ratio set in step S201. The set value of the fluorescence sensitivity Sir is calculated by Sir=Ro×Sw, where Ro represents the sensitivity ratio.

In step S208, the fluorescence sensitivity control circuitry 139 determines a control means of the fluorescence sensitivity based on the set value of the fluorescence sensitivity Sir. The fluorescence sensitivity is adjusted in accordance with the determined control means. The fluorescence sensitivity can be controlled by "exposure time×master gain value", similar to the background sensitivity. For example, in the case where the gain is controlled, the fluorescence sensitivity control circuitry 139 transmits to the gain adjustment circuitry 133 a control signal to control the gain so that the fluorescence sensitivity is to be equal to or close to the set value Sir of the fluorescence sensitivity. The gain adjustment circuitry adjusts the gain of the IR imaging signal based on the control signal.

In the case where the exposure time is controlled, the fluorescence sensitivity control circuitry 139 transmits to the imaging circuitry 11 a control signal to control the exposure time so that the fluorescence sensitivity is to be equal to or close to the set value of the fluorescence sensitivity. The shutter 115 of the imaging circuitry 11 controls the exposure time in accordance with the control signal.

In the case where the light amount is controlled, the fluorescence sensitivity control circuitry 139 transmits to the IR source 22 a control signal to control the light amount so that the fluorescence sensitivity is equal to or close to the set value of the fluorescence sensitivity. The IR source 22 emits light of the amount controlled in accordance with the control signal.

In step S209, the image superimposition circuitry 17 generates a composite image by the background image and the fluorescent image in which the sensitivity has been adjusted. The composite image is displayed on the display so that the user can confirm it.

After the fluorescence sensitivity is adjusted in step S209, the processing returns to step S203 to acquire subsequent imaging signals (RGB imaging signals, and IR imaging signal), and repeats each step.

For example, the background sensitivity, control circuitry 137 may be configured to include determination processing to determine whether or not the brightness of the background image has changed, and step S204 to step S209 may be performed only if the brightness has changed. That is, if the brightness has not changed, step S204 to step S209 which relate to the sensitivity adjustment are not performed. This realizes a reduction of power consumption. The determination processing to determine whether or not the brightness has changed may be performed after step S203, for example.

The sensitivity ratio may be set after the photometry area is determined. For example, it may be adopted that the image processing circuitry 13 stores the statistical correspondences between the subject (a target portion of the subject), the photometry area, and the sensitivity ratio, and the sensitivity ratio is determined based on the correspondences depending on the photometry area set in step S202.

The sensitivity ratio may be determined not only by manual setting of the user, but also by automatic setting. There may be a case where the sensitivity setting of the fluorescent image are obviously improper, for example, the case where the fluorescent image expands on the entire screen, or where the fluorescent image is not displayed on the screen. In such a case, the sensitivity ratio may be automatically adjusted by adjusting the fluorescence image to be within an appropriate range.

Specifically, in the case where the fluorescent image expands on the entire screen, a ratio of the fluorescence sensitivity to the background sensitivity is too high. Thus, the fluorescence sensitivity may be adjusted by the fluorescence sensitivity control circuitry 139 decreasing the fluorescence sensitivity to the upper limit of the acceptable range. The condition of the acceptable range may be defined by the size in which the range of the fluorescent image displayed on the screen is equal to or less than a threshold value, or the value in which the peak level of the brightness value of the fluorescent image is equal to or less than a threshold value.

On the other hand, in the case where the fluorescent image is not displayed on the screen, a ratio of the fluorescence sensitivity to the background sensitivity is too low. Thus, the fluorescent sensitivity adjusted by the fluorescence sensitivity control circuitry 139 increasing the fluorescent sensitivity to the lower limit of the acceptable range. The condition of the acceptable range may be defined by the size in which the range of the fluorescent image displayed on the screen is equal to or greater than a threshold value, or the value in which the peak level of the brightness value of the fluorescent image is equal to or greater than a threshold value. The condition of the acceptable range is not limited to the above, but may be defined by any means relating to the fluorescent sensitivity.

The sensitivity adjustment may be flexibly performed by allowing the sensitivity ratio to have a degree of variation in accordance with the fluorescent sensitivity within the acceptable range.

Next, the imaging sequence at the imaging circuitry 11 will be explained with reference to FIG. 3 and FIG. 4.

Figure 3:
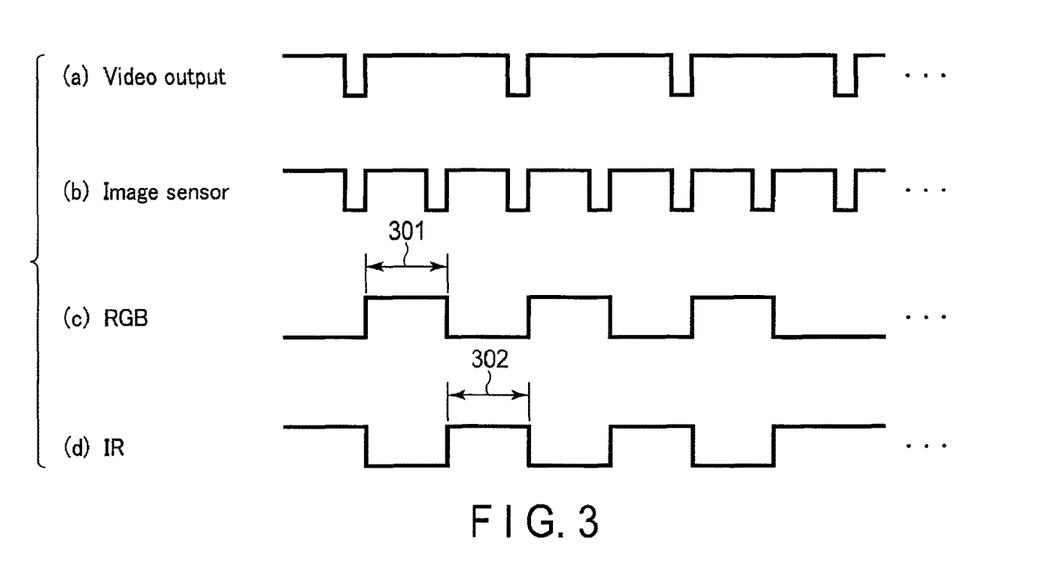
FIG. 3 illustrates an imaging sequence according to the first embodiment.

FIG. 3 illustrates timing charts of (a) video output, (b) exposure time for each image sensor, (c) output of white light (RGB) from the white light source 20, and (d) output of IR light from the IR source 22, from top to bottom.

As stated above, R light and fluorescence obtained by IR light are split in the same direction by the prism 111. Accordingly, the irradiation time by the white light source 20 and the irradiation time by the IR source 22 are switched in a time-division manner so that the R light and the fluorescence are individually received by the image sensors.

Specifically, in time period 301, the white light source 20 is turned on (white light is output), and the IR source 22 is turned off (IR light is not output). That is, only white light enters the prism 111. Accordingly, R light, G light, and B light are respectively received by the image sensors 116, 117, and 118.

In time period 302 subsequent to the time period 301, the white light source 20 is turned off, and the IR source 22 is turned on. That is, only fluorescence enters the prism 111. Accordingly, after the time period 301, fluorescence is received by the image sensor 119.

By repeating the aforementioned processing, an R-imaging signal, a G-imaging signal, a B-imaging signal, and an IR imaging signal can be acquired by using the prism 111 which splits the light into R light, G light, and B light.

Another example of the imaging sequence at the imaging circuitry 11 will be explained with reference to FIG. 4.

Figure 4:
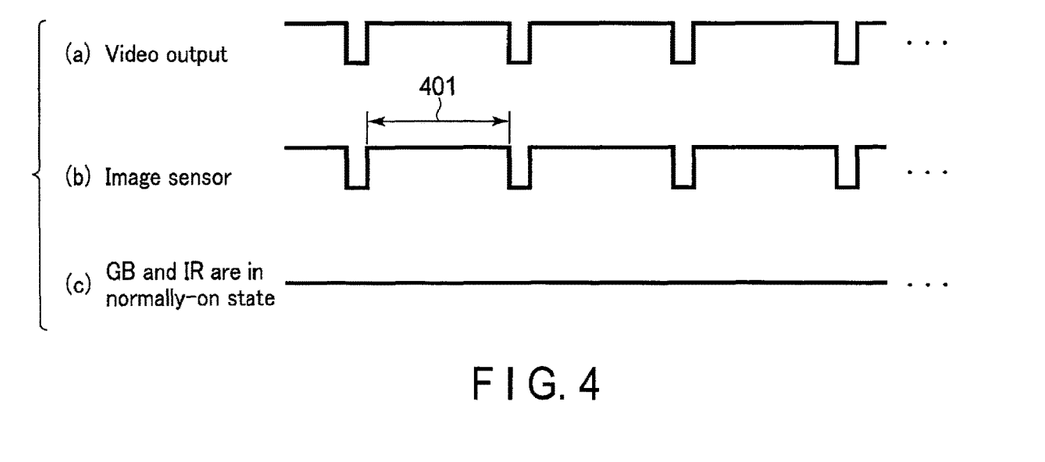
FIG. 4 illustrates another example of imaging sequence according to the first embodiment.

FIG. 4 illustrates timing charts of (a) video output, (b) exposure time for each image sensor, (c) output of GB light from the white light source 20, and (d) output of IR light from the IR source 22, from top to bottom.

In the example shown in FIG. 4, the light output from the white light source 20 is not RGB light. The white light source 20 outputs GB light in which R light components are attenuated by a color filter, etc. That is, the background image generated based on a G-imaging signal and a B-imaging signal obtained from the GB light is a black-and-white image, not a color image.

Specifically, the white light source 20 and the IR source 22 both are in a normally-on state, namely, GB light from the white light source 20 and IR light from the IR source 22 are applied simultaneously. During time period 401, the image sensors 117 and 118 can respectively receive G light and B light, and the image sensor 119 can receive fluorescence.

Accordingly, IR light can be received at the timing of receiving R light since the image is black-and-white, and it is not necessary to perform time division processing of R light and IR light, as shown in FIG. 3. Thus, it is possible to suppress a decrease of sensitivity due to shortening of the exposure time.

An example display of a composite image in which the sensitivity control processing has been performed according to the first embodiment will be explained with reference to FIG. 5.

Figure 5:
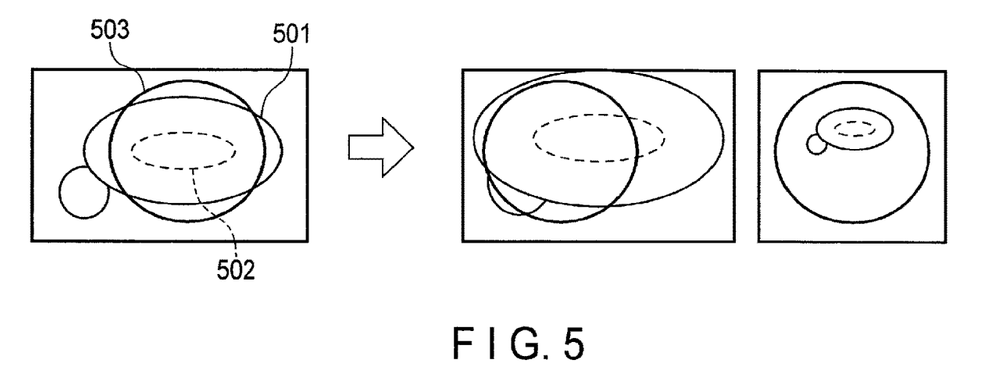
FIG. 5 illustrates a display example of a composite image after the sensitivity control processing is performed.

The left drawing in FIG. 5 is an example of a composite image in which a fluorescent image 502 by a fluorescence marker is superimposed onto a background image 501 of the subject imaged by an endoscope, for example. It is assumed here that the sensitivity ratio which is a reference in a photometry area 503 is set.

The middle drawing in FIG. 5 shows a case where a light source (white light source 20 and IR source 22) or the imaging circuitry 11 comes in close proximity to the subject.

In the case where the light source or the imaging circuitry 11 comes in close proximity to the subject, the incident light amount to the imaging circuitry 11 increases, and accordingly the brightness of both background image and fluorescent image increases. In the case where automatic adjustment of the background sensitivity is performed, the fluorescence sensitivity is set based on the background sensitivity and the sensitivity ratio. Accordingly, the fluorescence sensitivity can be automatically adjusted, for example, to allow the fluorescent image to be darker so as to maintain the sensitivity ratio constant.

On the other hand, the right drawing in FIG. 5 shows a case where the light source or the imaging circuitry 11 moves away from the subject.

In the case where the light source or the imaging circuitry 11 moves away from the subject, the incident light amount to the imaging circuitry 11 decreases, and accordingly the brightness of both background image and fluorescent image decreases. In this case, similar to the case where the light source or the imaging circuitry 11 comes in close proximity to the subject, the fluorescence sensitivity is set based on the background sensitivity and the sensitivity ratio. Accordingly, the fluorescence sensitivity can be automatically adjusted, for example, to allow the fluorescent image to be brighter so as to maintain the sensitivity ratio constant.

In the case where the light amount of the white light source 20 cannot be controlled, the background sensitivity control circuitry 137 may adjust the background sensitivity by controlling at least one of the exposure time or the gain. Similarly, in the case where the light amount of the IR source 22 cannot be controlled, the fluorescence sensitivity control circuitry 139 may adjust the fluorescence sensitivity by controlling at least one of the exposure time or the gain.

According to the aforementioned first embodiment, the fluorescence sensitivity is set based on the background sensitivity and the sensitivity ratio. With this structure, even in the case where the imaging conditions change due to the change in distance between the subject and the imaging apparatus or the light source, and the brightness of the background image is automatically adjusted, the brightness of the fluorescent image is automatically adjusted so as to maintain the sensitivity ratio between the background image and the fluorescent image constant.

Thus, even in the case where the distance between the subject and the imaging apparatus or the light source changes, there is no need to set the brightness of the background image with respect to the fluorescent image, and the user's desired sensitivity ratio and viewability can be maintained in the composite image. This improves user usability.

Second Embodiment

In the first embodiment, it is assumed that the light amount output from the light source is controllable. However, in the case where the light amount is not controllable, if the light amount of at least one of the white light source 20 or the IR source 22 changes, there is a possibility that the sensitivity ratio may be different from the set sensitivity ratio only by controlling the sensitivity ratio.

For example, if the light amount output from the white light source 20 becomes double, the gain is controlled to be ½ in the sensitivity adjustment of the background image. In this case, if the sensitivity ratio is controlled to be constant, the gain of the fluorescent image becomes ½ even though the light amount from the IR source 22 does not change. Accordingly, only the sensitivity of the fluorescent image decreases.

In the second embodiment, the desired sensitivity ratio can be maintained by referring not only to the sensitivity ratio, but also to the strength ratio between the white light source 20 and the IR source 22 when the sensitivity ratio is set.

Figure 6:
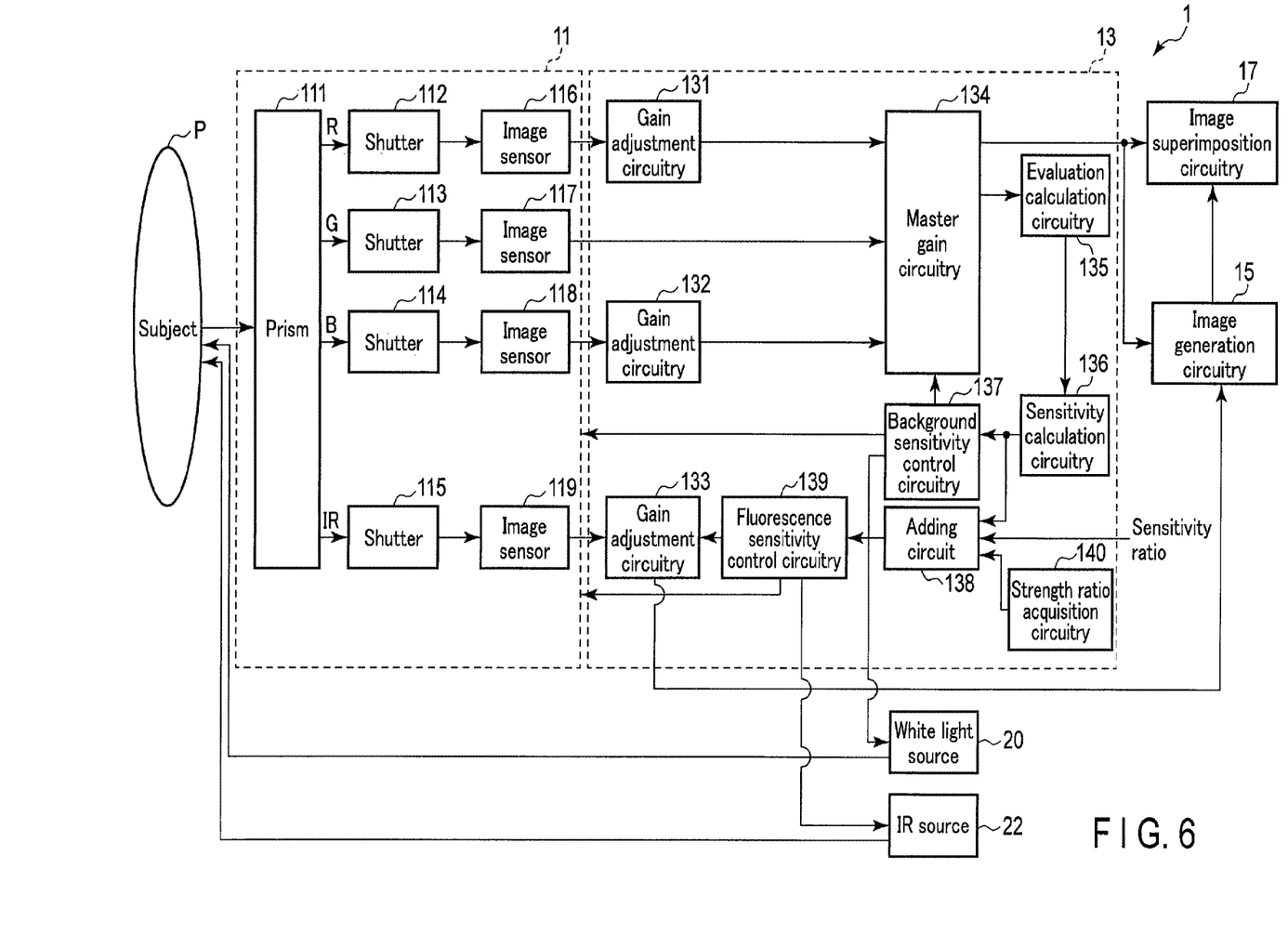
FIG. 6 is a block diagram of an imaging apparatus according to the second embodiment.

The imaging apparatus 1 according to the second embodiment will be explained with reference to the block diagram of FIG. 6.

The imaging apparatus 1 includes strength ratio acquisition circuitry 140 in addition to the elements according to the first embodiment.

The strength ratio acquisition circuitry 140 acquires the strength ratio when the sensitivity ratio is set. The strength ratio is a ratio between the strength (light amount) of white light and the strength (light amount) of IR light. The strength ratio is obtained, for example, based on the strength values received from the white light source 20 and the IR source 22 at the time when the user sets the sensitivity ratio, as described in the first embodiment. The strength ratio may be set by the user.

The adding circuit 138 respectively acquires the sensitivity ratio from outside, and the strength ratio from the strength ratio acquisition circuitry 140, and performs processing to maintain the sensitivity ratio constant by referring to the strength ratio. Specifically, the strength ratio Rlo is represented by "strength of white light/strength of IR light". The set value of fluorescence sensitivity Sir is represented by Sir=Sw×Ro×Rlt/Rlo, where Rlt represents the current strength ratio.

Thus, the adding circuit 138 can calculate the set value of the fluorescence sensitivity Sir by using the information of the strength ratio when calculating the sensitivity ratio.

The fluorescence sensitivity control circuitry 139 may determine a control means of the fluorescence sensitivity based on the set value of the fluorescence sensitivity from the adding circuit 138, and adjust the fluorescence sensitivity, in the similar manner to the first embodiment.

According to the aforementioned second embodiment, in the case where the light amount of the light source cannot be controlled, even if the strength ratio between the white light source and the IR light source changes, the sensitivity ratio between the background image and the fluorescent image can be maintained by calculating the fluorescence sensitivity in consideration of the strength ratio. This further improves usability.

In the aforementioned embodiments, since the dichroic prism is adopted, the white light source 20 and the IR source 22 are controlled by time division to acquire four imaging signals based on R light (IR light), G light, and B light. However, if a prism which can split light into four channels of R light, G light, B light and IR light is adopted, a signal can be read directly from each channel, and accordingly, there is no need to control the light source in a time-division manner.

It may also be possible to acquire R light, G light, and .B light by using a color filter instead of the prism 111. In addition, the imaging circuitry 11 may include the gain adjustment circuitry 131 and 132. The master gain circuitry 134 may be provided both in the imaging circuitry 11 and the image processing circuitry 13 so that the gain can be adjusted respectively. With such a structure, the gain may be adjusted in the image processing circuitry 13 after the gain is adjusted in the imaging circuitry 11 to compensate the gain amount.

In the present embodiments, near infrared radiation is assumed to be used; however, the same processing can be applied for the case where multiple types of light of other wavelength bands such as far-infrared radiation or ultraviolet rays are used.

If multiple types of fluorescence (for example, red and blue) of multiple wavelength bands are processed, the shutter 112 and the image sensor 116 are commonly used for R light and red fluorescence, and functions to the R light and the red fluorescence are divided by time division. The shutter 114 and the image sensor 118 are commonly used for B light and blue fluorescence, and they are processed in a time-division manner.

In addition, if fluorescence of multiple wavelength bands are used, when determining a second sensitivity ratio between the background image and fluorescence of a second wavelength band after determining a first sensitivity ratio between the background image and fluorescence of a first wavelength band, the fluorescence sensitivity control circuitry 139 may determine the second sensitivity ratio based on the first sensitivity ratio.

Furthermore, each of the aforementioned circuitry may be implemented by an ASIC (Application Specific Integrated Circuit), which includes hardware circuits specific to the function, an FPGA (Field Programmable Gate Array), a CPLD (Complex Programmable Logic Device), or an SPLD (Simple Programmable Logic Device).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An imaging apparatus comprising:
   an image sensor configured to generate a first electrical signal upon receiving first light, and to generate a second electrical signal upon receiving second light;
   image generation circuitry configured to successively generate a first image based on the first electrical signal, and to successively generate a second image based on the second electrical signal;
   calculation circuitry configured to calculate a first sensitivity value of the first image to allow brightness of the first image to be equal to a predetermined value or to be a value within a first range from the predetermined value, and to calculate a second sensitivity value of the second image relating to brightness of the second image based on the first sensitivity value and a predetermined ratio;
   superimposition circuitry configured to generate a composite image by superimposing (1) the second image in which the brightness is adjusted using the second sensitivity value onto (2) the first image in which the brightness is adjusted using the first sensitivity value; and
   acquisition circuitry configured to acquire a strength ratio between the first light and the second light when the predetermined ratio is set,
   wherein the calculation circuitry calculates the second sensitivity value based on the predetermined ratio and the strength ratio.

2. The apparatus according to claim 1, wherein the predetermined ratio is a ratio between the first sensitivity value and the second sensitivity value at a time phase.

3. The apparatus according to claim 1, wherein the predetermined ratio is a ratio between the first sensitivity value and the second sensitivity value at a time phase.

4. The apparatus according to claim 1, wherein the first sensitivity value includes at least one of a strength of the first light, an exposure time of the first light, and a gain value to be applied to the first electrical signal, and
   the second sensitivity value includes at least one of a strength of the second light, an exposure time of the second light, and a gain value to be applied to the second electrical signal.

5. The apparatus according to claim 1, wherein the first light is visible light, and the second light is fluorescent light.

6. The apparatus according to claim 1, further comprising control circuitry configured to control the predetermined ratio so that a condition of the adjusted second image is within an acceptable range when setting the predetermined ratio.

7. An imaging apparatus comprising:
   an image sensor configured to generate a first electrical signal upon receiving first light, and to generate a second electrical signal upon receiving second light;
   image generation circuitry configured to successively generate a first image based on the first electrical signal, and to successively generate a second image based on the second electrical signal;
   calculation circuitry configured to calculate a first sensitivity value of the first image to allow brightness of the first image to be equal to a predetermined value or to be a value within a first range from the predetermined value, and to calculate a second sensitivity value of the second image relating to brightness of the second image based on the first sensitivity value and a predetermined ratio; and
   superimposition circuitry configured to generate a composite image by superimposing (1) the second image in which the brightness is adjusted using the second sensitivity value onto (2) the first image in which the brightness is adjusted using the first sensitivity value,
   wherein the image sensor receives a plurality of types of the second light, and a first ratio between the first light and one of the plurality of types of the second light is used for determining each ratio between the first light and another type of the second light.

8. The apparatus according to claim 7, wherein the predetermined ratio is a ratio between the first sensitivity value and the second sensitivity value at a time phase.

9. The apparatus according to claim 7, wherein the first sensitivity value includes at least one of a strength of the first light, an exposure time of the first light, and a gain value to be applied to the first electrical signal, and
   the second sensitivity value includes at least one of a strength of the second light, an exposure time of the second light, and a gain value to be applied to the second electrical signal.

10. The apparatus according to claim 7, wherein the first light is visible light, and the second light is fluorescent light.

11. The apparatus according to claim 7, further comprising control circuitry configured to control the predetermined ratio so that a condition of the adjusted second image is within an acceptable range when setting the predetermined ratio.

12. An imaging method, comprising:
successively generating a first image based on a first electrical signal obtained by receiving first light, and successively generating a second image based on a second electrical signal obtained by receiving second light;
calculating a first sensitivity value of the first image to allow brightness of the first image to be equal to a predetermined value or to be a value within a first range from the predetermined value, and calculating a second sensitivity value of the second image relating to brightness of the second image based on the first sensitivity value and a predetermined ratio;
generating a composite image by superimposing (1) the second image in which the brightness is adjusted using the second sensitivity value onto (2) the first image in which the brightness is adjusted using the first sensitivity value;
acquiring a strength ratio between the first light and the second light when the predetermined ratio is set; and
calculating the second sensitivity value based on the predetermined ratio and the strength ratio.

13. An imaging method, comprising:
successively generating a first image based on a first electrical signal obtained by receiving first light, and successively generating a second image based on a second electrical signal obtained by receiving second light;
calculating a first sensitivity value of the first image to allow brightness of the first image to be equal to a predetermined value or to be a value within a first range from the predetermined value, and calculating a second sensitivity value of the second image relating to brightness of the second image based on the first sensitivity value and a predetermined ratio;
generating a composite image by superimposing (1) the second image in which the brightness is adjusted using the second sensitivity value onto (2) the first image in which the brightness is adjusted using the first sensitivity value;
receiving a plurality of types of the second light;
determining a first ratio between the first light and one of the plurality of types of the second light; and
determining respective ratios between the first light and another type of the second light using the first ratio.

* * * * *